US007815935B2

(12) United States Patent
Li et al.

(10) Patent No.: US 7,815,935 B2
(45) Date of Patent: Oct. 19, 2010

(54) ORALLY DISTINTEGRATING FORMULATION AND PROCESS FOR PREPARING THE SAME

(75) Inventors: Hewei Li, Beijing (CN); Hongfei Wang, Beijing (CN); Mingzhou Wang, Beijing (CN); Linyuan Wang, Beijing (CN)

(73) Assignee: Quantum Hi-Tech (Beijing) Research Institute, Beijing (CN)

( * ) Notice: Subject to any disclaimer, the term of this patent is extended or adjusted under 35 U.S.C. 154(b) by 249 days.

(21) Appl. No.: 11/568,474

(22) PCT Filed: Apr. 30, 2005

(86) PCT No.: PCT/CN2005/000616

§ 371 (c)(1),
(2), (4) Date: Nov. 29, 2006

(87) PCT Pub. No.: WO2005/105047

PCT Pub. Date: Nov. 10, 2005

(65) Prior Publication Data

US 2007/0092564 A1 Apr. 26, 2007

(30) Foreign Application Priority Data

Apr. 30, 2004 (CN) .................. 2004 1 0038822

(51) Int. Cl.
*A61K 9/48* (2006.01)
(52) U.S. Cl. ..................................... 424/451
(58) Field of Classification Search ................. 424/49, 424/48, 451; 514/1
See application file for complete search history.

(56) References Cited

U.S. PATENT DOCUMENTS

| | | | |
|---|---|---|---|
| 5,457,895 A | 10/1995 | Thompson et al. | |
| 2004/0101494 A1* | 5/2004 | Scott et al. | 424/49 |
| 2006/0188563 A1* | 8/2006 | Sato et al. | 424/451 |

FOREIGN PATENT DOCUMENTS

| | | |
|---|---|---|
| CN | 1394607 A | 2/2003 |
| CN | 1429618 A | 7/2003 |
| JP | 7157431 A | 6/1995 |
| JP | 8291051 A | 11/1996 |
| JP | 2002012541 A * | 1/2002 |
| WO | WO-0050013 A | 8/2000 |

OTHER PUBLICATIONS

The English abstract for JP 2002012541A (2002).*
International Search Report for International Application No. PCT/CN2005/000616, dated Sep. 1, 2005.

* cited by examiner

*Primary Examiner*—Kevin Weddington
(74) *Attorney, Agent, or Firm*—Junhe Law Offices P.C.; Zhaohui Wang

(57) ABSTRACT

An orally disintegrating formulation and its preparation are provided. The orally disintegrating formulation comprises an effective amount of a pharmaceutically active ingredient and a matrix, wherein the matrix contains an amino acid and pullulan. The orally disintegrating formulation can disintegrate rapidly in oral cavity and be taken without aid of water; Moreover, the formulation has a low hygroscopicity, so that the requirements for storing or producing the formulation is decreased, and the storage life is elongated to facilitate the administration by a patient and the preparation of the protein and vaccine drugs.

7 Claims, No Drawings ary
ORALLY DISINTEGRATING FORMULATION AND PROCESS FOR PREPARING THE SAME

CROSS-REFERENCE TO PRIOR APPLICATION

This is a U.S National Phase application under 35 U.S.C. §371 of International Application No. PCT/CN2005/000616, filed Apr. 30, 2005 and claims benefit of Chinese Patent Application No. 200410038822.5, filed Apr. 30, 2004, both of which are incorporated herein. The International Application was published in Chinese on Nov. 10, 2005 as WO2005/105047 A1 under PCT Article 21(2).

FIELD OF THE INVENTION

The present invention relates to an orally disintegrating formulation and a process for preparing the same. Particularly, the present invention relates to an orally disintegrating formulation comprising pullulan and amino acid, and a process for preparing the same.

BACKGROUND OF THE INVENTION

The term "Orally disintegrating formulation" used herein refers to those that rapidly disintegrate or dissolve in oral cavity. Such a formulation disintegrates rapidly and mostly dissolves upon contacting with saliva, which formulation will be swallowed by a patient thereafter. Its taste is palatable and no gritty feeling is perceived. The orally disintegrating formulation emerged in late 1970s, when Gregory et. al prepared a drug carrier with high porosity by freeze-drying. The carrier could disintegrate upon contacting with saliva in oral cavity. The orally disintegrating formulation becomes more and more popular for its special advantages, such as being swallowed without the aid of water and rapid disintegration in oral cavity, which provides convenience to the patients who have swallow difficulty or have no easy access to water.

Currently, the orally disintegrating formulation has been developed overseas which is prepared by using hydrolyzed gelatin able to disintegrate rapidly in water as the matrix of drug (U.S. Pat. No. 4,305,502) and releases active ingredients rapidly in oral cavity. It is well known that the orally disintegrating formulation has a broad drug-loaded range and hydrolyzed gelatin is used as carrier or matrix-forming agent of drug in a lot of rapidly releasing formulations. Typically, the hydrolyzed gelatin is characterized in that it can enhance the hardness of the formulation and prevent the formulation from crashing when released from the package.

Gelatin mostly comes from hydrolyzed product of the animal collagen tissues, such as skin, tendon, ligament and bones. It is a common technique to apply hydrolyzed gelatin as a drug carrier and matrix-forming agent. But in recent years, the emerge of the animal origin diseases, such as mad cow disease, foot and month disease, scrapie and the like, results in more and more doubts as to the safety of hydrolyzed gelatin. Moreover, gelatin product obtained from pigs could't be acceptable by the Muslim people and people with other religions, and gelatin product obtained from animal is also unacceptable by vegetarians.

It is difficult to apply hydrolyzed gelatin as an excipient in the preparation process. Firstly, in order to sufficiently dissolve the hydrolyzed gelatin, it is necessary to heat the hydrolyzed gelatin, and the producing process using hydrolyzed gelatin as an excipient needs a heating-step. As a result, it not only prolongs the preparation period of orally disintegrating formulation, but also increases the cost. In the traditional process, it is necessary to keep the mixture containing hydrolyzed gelatin for a longer time to make the liquid system disperse homogeneously. But the viscosity of the mixture of hydrolyzed gelatin acting as an excipient increases with time, causing more difficulties to process. Moreover, in the sublimation-drying process, the hydrolyzed gelatin is inclined to forming a dense film on the surface of the formulation, which is not completely dried, thus preventing the moisture from further sublimating from the inner part of the formulation and drying. Therefore, the subsequent drying process becomes more complicate, which in turn increases the production cost. Furthermore, the elevation of the product temperature will destroy the unstable active ingredient.

Another problem encountered through using the hydrolyzed gelatin is the narrow scope of the active ingredient used in the formulation. Because hydrolyzed gelatin has some properties of protein and polypeptide, it is not suitable to use it in formulation containing an active ingredient which is apt to react with protein and polypeptide. Therefore, the utility of the hydrolyzed gelatin is limited when being used in the formulation of a compound drug with more phenol and hydroxyl groups, traditional Chinese medicine and its active ingredient, such as the soluble salvianolate, as well as other soluble ingredients containing tannins in traditional Chinese Medicine.

As a solution to the above problems, pullulan has been proposed abroad (WO 00/50013) to be used instead of hydrolyzed gelatin as the binder of the orally disintegrating formulation to produce orally disintegrating formulation. Although the solution overcomes the drawbacks of the orally disintegrating formulation using hydrolyzed gelatin as the binder, because a saccharide or alditol is used in the orally disintegrating formulation as the matrix-forming agent and has high hygroscopicity, the formulation is easy to absorb moisture of the air in the manufacturing process, which leads to partial or complete collapse of the matrix structure and a longer disintegrating time. Furthermore, the formulation shrinks due to the hygroscopicity and the appearance of formulation becomes grotty, which results in detest of the consumer in the vision. Even more severely, such a formulation is forbidden coming into the market for its quality is not in conformity with the Quality Standard. To solve this problem, a process was brought forward, i.e., the traditional orally disintegrating formulation is air tightly sealed using double aluminum packing materials, by which, the formulation is kept away from the moisture of the air. However, the process only provides a temporary solutions rather than a final solution. Not only is a great deal of aluminum material used, resulting in the resource waste, but also the cost of the formulation increases. Furthermore, even if using the aluminum package, a patient, when taking the formulation from the package, usually feels uncomfortable as the formulation adheres to the hands due to the high hygroscopicity. This takes place more usually in summer. Therefore, there is an urgent need for a new formulation which can overcome the defects brought by the using of the hydrolnyzed gelatin as a binder, at the same time, the hygroscopicity of which is lower as compared with the disintegrating formulation using saccharide or alditol as a matrix-forming agent, and the appearance and the disintegrating time of which is not affected by the moisture of the air.

Besides, if the active ingredient is a protein or a polypeptide drug, the structure of the active ingredient will be destroyed by the mechanical effects produced in the freezing process and its activity will be decreased.

In order to solve the above-mentioned problems, the inventors of the present invention has done extensive research and completed the invention.

DETAILED DESCRIPTION OF THE INVENTION

An object of the invention is to provide an orally disintegrating formulation, which is not affected by the safety of the animal and cost-effective, especially, a formulation which does not absorb the moisture in the air and consequently has a longer shelf-term.

Furthermore, amino acids are used as the matrix-forming agent in the formulation of the invention, wherein the amino acids can decrease the mechanical effect in the freezing process, and thereby protecting the structure of the active ingredient, such as a protein or polypeptide, as compared with the saccharide or alditol.

Another object of the invention is to provide a process for preparing the above-mentioned orally disintegrating formulation.

After having studied for several years, the inventor of the invention has developed an orally disintegrating formulation which meets the above requirements, and its preparation, and thereby completed the invention.

The orally disintegrating formulation of the invention comprises an effective amount of a pharmaceutically active ingredient and a matrix, wherein the matrix comprises a amino acid as the matrix-forming agent and pullulan as the binder.

The amount of the pharmaceutically active ingredient in the orally disintegrating formulation of the invention is not particularly limited and may be suitably selected, depending on the various physical and chemical properties of the active ingredient and the single dose needed by the patient. The amount can be, for example, 0.1-99% (w/w), preferably 1-70% (w/w), more preferably 10-80% (w/w), especially preferably 20~80% (w/w), and most preferably 20-70% (w/w).

The ratio by weight of the amino acid to pullulan in the matrix is preferably 0.1-10, more preferably 0.17-5.5, especially preferably 0.5-1.5.

The orally disintegrating formulation of the invention, when desired, may further comprises other pharmaceutically acceptable excipients, for example, thickening agent, stabilizer, surfactant, antioxidant, sweeteners, flavoring agent, taste-masking agent, coloring agent, transdermal absorption enhancer, pH modifying agent, bacteriostatic agent and so on.

As the amino acid contained in the formulation of the invention, it is preferably selected from the group consisting of glycine, serine, arginine, and a mixture thereof, more preferably glycine.

In the formulation of the invention, when the effective dose of pharmaceutically active ingredient is not soluble in the solvent, a thickening and suspending agent is further included to make the active ingredient disperse more homogeneously in the formulation.

The thickening and suspending agent is selected from the group consisting of xanthum gum, konjac gum, gum of natural source, synthetical polymer compound, polypeptide, polysaccharide and a mixture thereof, preferably xanthum gum, konjac gum and a mixture thereof. The gum of natural source is selected from the group consisting of dextran, alginate gum, arabic gum, guar gum, agar, HMC, carrageenan, pectin and a mixture thereof. The synthetical polymer is polyvinyl pyrrolidone (PVP).

In another aspect, the invention relates to a process for preparing the orally disintegrating formulation, comprising steps of:

(a) formulating the pharmaceutically active ingredient, pullulan, amino acid and solvent into a solution or suspension;

(b) freezing the solution or suspension at a low temperature;

(c) freeze-drying the formulation obtained in step (b) to remove the solvent and the solid formulation is obtained.

The amino acid is preferably selected from the group consisting of glycine, serine, arginine, and a mixture thereof, more preferably glycine.

As the pharmaceutically active ingredient in the orally disintegrating formulation of the invention is not soluble in the water, a thickening and suspending agent is further added into the solution or suspension formed in step (a) so as to promote active ingredient disperse more homogeneously in the formulation.

The used ratio by weight of the amino acid to pullulan in the above process is preferably from 0.1 to 10, more preferably from 0.17 to 5.5, especially preferably from 0.5 to 1.5.

Any conventional process can be used to mix the pharmaceutically active ingredient, pullulan, and amino acid, as long as a solution or suspension is homogeneously formulated, for example by magnetic stirring, mechanical stirring and homogenizer, preferably homogenizer.

A degas step may be used before the formulated solution or suspension is frozen, if necessary. The degas step may use any degas methods, such as vacuum pump direct degas, ultrasonic oscillation degas, sweeping degas by inert gas and on-line degas.

The thickening and suspending agent is selected from the group consisting of xanthum gum, konjac gum, gum of natural source, synthetical polymer compound, polypeptide, polysaccharide and a mixture thereof, preferably xanthum gum, konjac gum and a mixture thereof. The gum of natural source is selected from the group consisting of dextran, alginate gum, arabic gum, guar gum, agar, HMC, carrageenan, pectin and a mixture thereof. The synthetical polymer compound is polyvinyl pyrrolidone.

In step (b) of the above process, the low temperature is preferably from −80° C. to −150° C. and the time for freezing is from 1 to 10 minutes. The freezing process may be any process known to the person skilled in the art, such as using turbine Expansion Engine, CFC, liquid nitrogen, as long as the temperature is kept from −80° C. to −150° C., and the time is kept from 3 to 10 minutes, preferably using liquid nitrogen.

In step (c) of the above process, the freeze-drying temperature is from −30° C. to 30° C., preferably from −20° C. to 20° C. The time for freeze-drying is from 1 to 10 hours, preferably 2 to 8 hours. The vacuum is from 0.01 mbar to 10 mbar, preferably from 0.01 mbar to 1 mbar.

The pharmaceutically active ingredient useful for the orally disintegrating agent of the invention is not specially limited. It may be any one or more drugs selected from the group consisting of:

Chemical drugs

Analgesic and anti-inflammatory drugs, such as Morphine, Buprehorphine, Rotundine, Probenecid and Caffeine.

Anti-migraine drugs, such as Zolmitriptan, Sumatriptan, and Dihydroergotamine.

Other analgesics, such as Tramadol Hydrochloride.

Anti-depressant drugs, such as Fluoxetine Hydrochloride, Venlafaxine, and Paroxetine.

Anti-anxiety drugs, Sedatives, Hypnotics, tranquilizer, Anti-epileptics, such as Olanzapine, Penfluridol, and Risperidone.

Anti-parkinson's drugs, such as Levodopa, Pregolide, and Bromocriptine.

Cholinesterase inhibitors, such as Hyoscine.

Other nervous system drugs, such as Hyperzine, and Cerebrolysin.

Adrenomimetics, such as Midodrine, and Dopamine.

Adrenoceptor blockers, such as Acebutolol, and Alprenolol

Anti-arrhythmic drugs, such as Amiodarone, Disopyramide and Cyclovirobuxine

Cardiotonic drugs, such as digoxin, and lanatoside C.

Anti-hypertensive drugs, such as Umlodipine, and Manidipine.

Lipid-modulating agents, such as Lovastatin.

Anti-anginal agents, such as Nitroglycerin, and Isosorbide mononitrate.

Other cardiovascular drugs, such as Rutin, and Creatine Phosphate.

Endocrine System Drugs:

Corticosteroid drugs, such as Betamethasone, and Cortisone Acetate.

Anti-Diabetic Agents, such as Repaglinede.

Antithyroid drugs, such as Propylthiouracil, Carbimazole, and Thiamazole.

Antihistamine drugs, such as Cetirizine hydrochloride, and Loratadine.

Autacoids, such as Dinoprostone, Alprostadil, and Betahistine.

Protein, peptide and recombinant drugs, such as Insulin, Glucagons, Growth Hormone polypeptide and their derivative.

Anesthetics, such as Desflurane, and Enflurane.

Nutrients, such as various amino acids and various vitamins.

Respiratory System drugs, such as Pentoxyrerine Citrate, Sabutamonl Sulfate, Montelukast, and Zafirlakast.

Digestive System drugs, such as Hyoscine Butylbromide, and Granisetron Hydrochloride.

Blood System drugs, such as EPO, Cobamamide.

Urinary System drugs, such as Azosemide, and Furosemide.

Genital System drugs, such as estrogens, and nandrolone phenylpropionate.

Anti-parasite drugs, such as Albendazole, and Cambendazole.

Anti-neoplastic drugs, such as Aminoglutethimide, and Amsacrine.

Anti-microbial drugs, such as Ampicilin, and Sulbenicillin Sodium.

Others, such as Sidenafil Citrate.

Oral vaccines, such as vaccine against Flu, and Tuberculosis.

Vaccines for the prevention and alleviation of a disease induced by a microorganism, such as *Vibrio,* and *Salmonella.*

Vaccines against a non-contagious immune modulating disease, such as hay fever, asthma, rheumatoid arthritis, and cancer.

Vaccines directly against veterinary diseases, such as Newcastle Disease, Feline Leukemia, Atrophic rhinitis, Erysipelas, Foot and Mouth diseases.

Active ingredients from Chinese herb, such as Breviscapine, and Arteannuin.

Single extracts from Chinese herb, such as Tanschinone, and Salrianolic acid.

Extracts from traditional Chinese medicine, such as extracts from composite salivia pellet, and extracts from composite Niu Huang Shang Qing Wan.

The orally disintegrating formulation of the present invention can completely disintegrate in oral cavity without the aid of water, so it is especially suitable for some special populations (such as the elders, patients laying up for a long time and vomiting seriously). Besides, because the orally disintegrating formulation of the invention can rapidly disintegrate in oral cavity, the effective area of the drug increases, which causes the speed of dissolution of the drug increase and the drug take effect more rapidly. It is especially of importance that the orally disintegrating formulation is not affected by the moisture in the air. The formulation does not absorb the moisture in the air and shrinks even if in the hot and humid atrocious environment. At the same time, it does not need to add a collapse protecting agent. As a result, it is unnecessary to decrease the humidity in environment with extra equipments during the process of preparing the orally disintegrating formulation of the invention. The appearance and quality of the prepared formulations are nearly unchanged even exposed to an environment with very high humidity, and the disintegrating time will not extend as the prolonged time of exposing in the air. Furthermore, the shelf life is longer than the conventional disintegrating formulations. Moreover, when a patient needs to take a medicine, he removes the medicine from the blister, and if the hygroscopicity of the medicine is too high, the medicine is apt to adhere to the hand. This situation typically occurs in humid summer. The orally disintegrating formulation of the invention, however, will not cause the above problem because of its low hygroscopicity.

CONCRETE MODE FOR CARRYING OUT THE INVENTION

The invention will be explained in detail by the following examples and comparative examples, and is not limited to these examples.

In the following examples and comparative examples, the assessment methods of the invention are as follows:

1) Time of Disintegrating

The Standing Tube Method is used to determine the disintegrating time of the orally disintegrating formulation, with the detailed procedures as follows:

The purified water of 37° C. is added into a glass test-tube with a diameter of 1.5 cm, and then the orally disintegrating formulation of the invention is added to the water. The time counted from the contact of formulation with water to the completion dispersion of the formulation is the disintegrating time of the formulation.

2) Hygroscopicity Assay

The hygroscopicity of the orally disintegrating formulation is tested, with the detailed procedures as follows:

A constant temperature and humidity incubator (Guangdong Medical Device Plant, LRH-250-S) is adjusted to 25° C. with RH of 90%. 60 tablets of prepared blank orally disintegrating formulations are weighted, put into a dried watch glass, and placed in the constant temperature and humidity incubator. A sample is taken out every 24 hours and weighted, which lasts for six consecutive days. The appearance change of the formulations is observed and the percent change of weight of the formulation is calculated respectively.

3) Appearance of the Formulation

The prepared formulation is taken out of the blister package by applying force upward from the bottom of the aluminum blister using fingers. Then the appearance, smoothness of the formulation, as well as the existence of dent, crackle are observed.

4) Hardness is divided into three degrees, which are respectively denoted by:

A: very high hardness

B: a little hardness and elasticity

C: easily cracked

EXAMPLE 1

| | |
|---|---|
| Rotundine | 30 mg |
| Pullulan | 8.8 mg |
| Glycine | 8.0 mg |
| Xanthan gum | 0.4 mg |
| Purified water | 352.8 mg |

An appropriate amount of purified water was added after the glycine (Beijing Jingqiu Chemical Co., Ltd) and pullulan (Hayashibara Co., Ltd, Japan) in above indicated amount were mixed homogeneously, and sufficiently stirred the whole so as to completely dissolve them at room temperature. After Xanthan gum (Beijing Shenhua Pharmaceutical Co., Ltd.) was sufficiently swelled with purified water, rotundine (Guangxi Hedic Top Pharmaceutical Co., Ltd.) was added and mixed homogeneously, and then homogeneously mixed with the above prepared solution of glycine and pullulan. Appropriate water was added with the total amount of the totally added purified water of 352.8 mg, and thus a drug solution was obtained. The drug solution was degassed by ultra-sonic oscillation degas and precisely dipped into a 1 ml mould using an electro-pipet gun (720110\710040), and after freezing at −110° C. for 5 minutes by spraying of the liquid nitrogen (Beijng Praxair, Inc. XL-45), it was transferred in a freeze-drying machine (Beijing Suyuan ZhongTian Science And Technology Co. Ltd, GLZ-0.8) and freeze-dried for 5 hours under the condition of 0.5 mbar with a temperature of −20° C. to 25° C.

EXAMPLE 2

| | |
|---|---|
| Breviscapine | 20 mg |
| Pullulan | 14 mg |
| Glycine | 12 mg |
| Xanthan gum | 0.28 mg |
| Purified water | 353.72 mg |

The process of example 1 as described above was repeated for the above components in the indicated amounts, except for using breviscapine instead of rotundine, and an orally disintegrating formulation of breviscapine was prepared. The test results were described in table 1.

EXAMPLE 3

| | |
|---|---|
| Loratadine | 10 mg |
| Pullulan | 4.4 mg |
| Glycine | 4.0 mg |
| Xanthan gum | 0.1 mg |
| Purified water | 181.5 mg |

The process of example 1 as described above was repeated for the above components in the indicated amounts, except for using loratadine instead of rotundine, and an orally disintegrating formulation of loratadine was prepared. The test results were described in table 1.

EXAMPLE 4

| | |
|---|---|
| Itopride hydrochloride | 50 mg |
| Pullulan | 15 mg |
| Glycine | 10 mg |
| Xanthan gum | 0.5 mg |
| Purified water | 424.5 mg |

The process of example 1 as described above was repeated for the above components in the indicated amounts, except for using itopride hydrochloride instead of rotundine, and an orally disintegrating formulation of itopride hydrochloride was prepared. The test results were described in table 1.

EXAMPLE 5

| | |
|---|---|
| Fluoxetine hydrochloride | 20 mg |
| Pullulan | 19 g |
| Glycine | 10 mg |
| Xanthan gum | 0.28 mg |
| Purified water | 350.72 mg |

The process of example 1 as described above was repeated for the above components in the indicated amounts, except for using fluoxetine hydrochloride instead of rotundine, and an orally disintegrating formulation of fluoxetine hydrochloride was prepared. The test results were described in table 1.

EXAMPLE 6

| | |
|---|---|
| Zolmitriptan | 2.5 mg |
| Pullulan | 12.4 mg |
| Glycine | 5 mg |
| Xanthan gum | 0.1 mg |
| Purified water | 180 mg |

The process of example 1 as described above was repeated for the above components in the indicated amounts, except for using Zolmitriptan instead of rotundine, and an orally disintegrating formulation of Zolmitriptan was prepared. The test results were described in table 1.

EXAMPLE 7

| | |
|---|---|
| Repaglinide | 0.5 mg |
| Pullulan | 4 mg |
| Glycine | 22 mg |
| Xanthan gum | 0.1 mg |
| Purified water | 173.4 mg |

The process of example 1 as described above was repeated for the above components in the indicated amounts, except for using repaglinide instead of rotundine, and an orally disintegrating formulation of repaglinide was prepared. The test results were described in table 1.

EXAMPLE 8

| | |
|---|---|
| Montelukast sodium | 4 mg |
| Pullulan | 4.9 mg |
| Glycine | 18 mg |
| Xanthan gum | 0.1 mg |
| Purified water | 163 mg |

The process of example 1 as described above was repeated for the above components in the indicated amounts, except for using montelukast sodium instead of rotundine, and an orally disintegrating formulation of montelukast sodium was prepared. The test results were described in table 1.

EXAMPLE 9

| | |
|---|---|
| Sildenafil citrate | 25 mg |
| Pullulan | 7.8 mg |
| Glycine | 12 mg |
| Xanthan gum | 0.2 mg |
| Purified water | 355 mg |

The process of example 1 as described above was repeated for the above components in the indicated amounts, except for using sildenafil citrate instead of rotundine, and an orally disintegrating formulation of sildenafil citrate was prepared. The test results were described in table 1.

EXAMPLE 10

| | |
|---|---|
| Apomorphine | 2 mg |
| Pullulan | 12 mg |
| Glycine | 2 mg |
| Xanthan gum | 0.2 mg |
| Purified water | 383.8 mg |

The process of example 1 as described above was repeated for the above components in the indicated amounts, except for using apomorphine instead of rotundine, and an orally disintegrating formulation of apomorphine was prepared. The test results were described in table 1.

EXAMPLE 11

| | |
|---|---|
| Salbutamol sulphate | 2 mg |
| Pullulan | 8 mg |
| Glycine | 12 mg |
| Purified water | 378 mg |

The above amounts of glycine (Beijing Jingqiu Chemical Co., Ltd), pullulan (Hayashibara Co., Ltd, Japan) and Salbutamol sulphate (Eternwin chemicals (china), Ltd.) were mixed homogeneously, and then the above amount of purified water was added to obtain a drug solution. The drug solution was precisely dipped into a 1 ml mould using an electro-pipet gun (720110\710040) with stirring, and after freezing at −90° C. for 10 minutes by spraying the liquid nitrogen (Beijng Praxair, Inc. XL-45), it was transferred in a freezing-drying machine (Beijing Suyuan ZhongTian Science And Technology Co. Ltd, GLZ-0.8) and freeze-dried for 7 hours under the conditions of 0.05 mbar with a temperature of −20° C. to 10° C.

EXAMPLE 12

| | |
|---|---|
| Zolpidem Tartrate | 5 mg |
| Pullulan | 5 mg |
| Glycine | 4 mg |
| Purified water | 186 mg |

The process of example 11 as described above was repeated for the above components in the indicated amounts, except for using zolpidem tartrate instead of Salbutamol sulphate, and an orally disintegrating formulation of zolpidem tartrate was prepared. The test results were described in table 1.

EXAMPLE 13

| | |
|---|---|
| Repaglinide | 5 mg |
| Pullulan | 2 mg |
| Serine | 10 mg |
| Xanthum gum | 0.2 mg |
| Purified water | 382.8 mg |

The process of example 1 as described above was repeated for the above components in the indicated amounts, except for using repaglinide instead of rotundine and serine instead of glycine, and an orally disintegrating formulation of repaglinide was prepared. The test results were described in table 1.

EXAMPLE 14

| | |
|---|---|
| Lovastatin | 20 mg |
| Pullulan | 8 mg |
| Serine | 8 mg |
| Xanthum gum | 0.2 mg |
| Purified water | 363.8 mg |

The process of example 1 as described above was repeated for the above components in the indicated amounts, except for using Lovastatin instead of rotundine and serine instead of glycine, and an orally disintegrating formulation of Lovastatin was prepared. The test results were described in table 1.

EXAMPLE 15

| | |
|---|---|
| Granisetron Hydrochloride | 1 mg |
| Pullulan | 2 mg |
| Serine | 2.5 mg |
| Purified water | 94.5 mg |

The process of example 11 as described above was repeated for the above components in the indicated amounts, except for using Granisetron Hydrochloride instead of Salbutamol sulphate, and an orally disintegrating formulation of Granisetron Hydrochloride was prepared. The test results were described in table 1.

EXAMPLE 16

| | |
|---|---|
| Tropisetron Hydrochloride | 5 mg |
| Pullulan | 12 mg |
| Serine | 3 mg |
| Purified water | 380.0 mg |

The process of example 11 as described above was repeated for the above components in the indicated amounts, except for using Tropisetron Hydrochloride instead of Salbutamol sulphate and serine instead of glycine, and an orally disintegrating formulation of Tropisetron Hydrochloride was prepared. The test results were described in table 1.

EXAMPLE 17

| | |
|---|---|
| Pergolide | 1 mg |
| Pullulan | 10 mg |
| Arginine | 12 mg |
| Xanthum gum | 0.28 mg |
| Purified water | 356.72 mg |

The process of example 1 as described above was repeated for the above components in the indicated amounts, except for using pergolide instead of rotundine and arginine instead of glycine, and an orally disintegrating formulation of pergolide was prepared. The test results were described in table 1.

EXAMPLE 18

| | |
|---|---|
| Cetirizine Hydrochloride | 10 mg |
| Pullulan | 4 mg |
| Arginine | 12 mg |
| Xanthum gum | 0.28 mg |
| Purified water | 363.72 mg |

The process of example 1 as described above was repeated for the above components in the indicated amounts, except for using Cetirizine Hydrochloride instead of rotundine and arginine instead of glycine, and an orally disintegrating formulation of Cetirizine Hydrochloride was prepared. The test results were described in table 1.

EXAMPLE 19

| | |
|---|---|
| Tramadol Hydrochloride | 50 mg |
| Pullulan | 10 mg |
| Arginine | 2 mg |
| Xanthum gum | 0.3 mg |
| Purified water | 337.7 mg |

The process of example 1 as described above was repeated for the above components in the indicated amounts, except for using Tramadol Hydrochloride instead of rotundine and arginine instead of glycine, and an orally disintegrating formulation of Tramadol Hydrochloride was prepared. The test results were described in table 1.

EXAMPLE 20

| | |
|---|---|
| Zolpidem Tartrate | 10 mg |
| Pullulan | 5 mg |
| Arginine | 3 mg |
| Purified water | 182 mg |

The process of example 11 as described above was repeated for the above components in the indicated amounts, except for using Zolpidem Tartrate instead of Salbutamol sulphate and arginine instead of glycine, and an orally disintegrating formulation of Zolpidem Tartrate was prepared. The test results were described in table 1.

EXAMPLE 21

| | |
|---|---|
| Olanzapine | 5 mg |
| Pullulan | 10 mg |
| Glycine | 6 mg |
| Serine | 2 mg |
| Xanthum gum | 0.2 mg |
| Purified water | 374.8 mg |

The process of example 1 as described above was repeated for the above components in the indicated amounts, except for using Olanzapine instead of rotundine and glycine plus serine instead of glycine, and an orally disintegrating formulation of Olanzapine was prepared. The test results were described in table 1.

EXAMPLE 22

| | |
|---|---|
| Granisetron Hydrochloride | 1 mg |
| Pullulan | 10 mg |
| Glycine | 8 mg |
| Arginine | 3 mg |
| Purified water | 178.0 mg |

The process of example 11 as described above was repeated for the above components in the indicated amounts, except for using Granisetron Hydrochloride instead of rotundine and glycine plus serine instead of glycine, and an orally disintegrating formulation of Granisetron Hydrochloride was prepared. The test results were described in table 1.

EXAMPLE 23

| | |
|---|---|
| Cyclovirobuxine | 1 mg |
| Pullulan | 10 mg |
| Serine | 4 mg |
| Arginine | 5.5 mg |
| Xanthum gum | 0.2 mg |
| Purified water | 179.3 mg |

The process of example 1 as described above was repeated for the above components in the indicated amounts, except for using Cyclovirobuxine instead of rotundine and the mixture of arginine and serine instead of glycine, and an orally disintegrating formulation of Cyclovirobuxine was prepared. The test results were described in table 1.

TABLE 1

|  | Example 1 | Example 2 | Example 3 | Example 4 | Example 5 | Example 6 |
|---|---|---|---|---|---|---|
| Disintegrating time (s) | 4 | 4 | 3 | 3 | 4 | 5 |
| Disintegrating state | rapidly disperse | rapidly disperse | rapidly disperse | rapidly disperse | rapidly disperse | rapidly disperse |
| Hygroscopicity | no obvious hygroscopicity | no obvious hygroscopicity | no obvious hygroscopicity | no obvious hygroscopicity | no obvious hygroscopicity | no obvious hygroscopicity |
| Hardness | A | A | A | A | A | A |
| Appearance | flat, smooth no dent | flat, smooth no dent | flat, smooth no dent | flat, smooth no dent | flat, smooth no dent | flat, smooth no dent |
| Adherence to wall | no | no | no | no | no | no |

|  | Example 7 | Example 8 | Example 9 | Example 10 | Example 11 | Example 12 |
|---|---|---|---|---|---|---|
| Disintegrating time (s) | 5 | 6 | 7 | 5 | 6 | 5 |
| Disintegrating state | rapidly disperse | rapidly disperse | rapidly disperse | rapidly disperse | rapidly dissolve | rapidly dissolve |
| Hygroscopicity | no obvious hygroscopicity | no obvious hygroscopicity | no obvious hygroscopicity | no obvious hygroscopicity | no obvious hygroscopicity | no obvious hygroscopicity |
| hardness | A | A | A | A | A | A |
| appearance | flat, smooth no dent | flat, smooth no dent | flat, smooth no dent | flat, smooth no dent | flat, smooth no dent | flat, smooth no dent |
| Adherence to wall | no | no | no | no | no | no |

|  | Example 13 | Example 14 | Example 15 | Example 16 | Example 17 |
|---|---|---|---|---|---|
| Disintegrating time (s) | 4 | 5 | 5 | 4 | 6 |
| Disintegrating state | rapidly dissolve | rapidly dissolve | rapidly disperse | rapidly dissolve | rapidly disperse |
| Hygroscopicity | no obvious hygroscopicity | no obvious hygroscopicity | no obvious hygroscopicity | no obvious hygroscopicity | no obvious hygroscopicity |
| Hardness | A | A | A | A | A |
| Appearance | flat, smooth no dent | flat, smooth no dent | flat, smooth no dent | flat, smooth no dent | flat, smooth no dent |
| Adherence to wall | no | no | no | no | no |

|  | Example 18 | Example 19 | Example 20 | Example 21 | Example 22 | Example 23 |
|---|---|---|---|---|---|---|
| Disintegrating time (s) | 4 | 5 | 5 | 4 | 5 | 4 |
| Disintegrating state | rapidly dissolve | rapidly dissolve | rapidly disperse | rapidly dissolve | rapidly disperse | rapidly dissolve |
| Hygroscopicity | no obvious hygroscopicity | no obvious hygroscopicity | no obvious hygroscopicity | no obvious hygroscopicity | no obvious hygroscopicity | no obvious hygroscopicity |
| Hardness | A | A | A | A | A | A |
| Appearance | flat, smooth no dent | flat, smooth no dent | flat, smooth no dent | flat, smooth no dent | flat, smooth no dent | flat, smooth no dent |
| Adherence to wall | no | no | no | no | no | no |

Because the hygroscopicity of mannitol is the lowest among all the saccharides and alditols, the inventors of the invention used mannitol (representing all saccharides and alditols) as the matrix-forming agent to prepare the orally disintegrating formulation and compared it with those of the present invention wherein amino acids were used as the matrix-forming agents.

According to the ingredients in the amount listed in table 2 below, a blank orally disintegrating formulation was prepared by the process of the invention. 60 tablets of the orally disintegrating formulations prepared in example 24 and comparative examples 1 to 5 were weighted respectively and then placed on the dried watch glass and incubated in an incubator with a constant temperature of 25° C. and 90% RH. The samples were taken out every 24 hours and weighted, for 6 consecutive days. The appearance changes of the formulations were observed and the percent weight changes were respectively calculated. The test results were shown in table 3 and the results of observation were shown in table 4.

TABLE 2

| | Excipients | Example 24 | Comparative example 1 | Comparative example 2 | Comparative example 3 | Comparative example 4 | Comparative example 5 |
|---|---|---|---|---|---|---|---|
| binder (mg) | pullulan | 16 | 16 | | | | |
| | hydrolyzed gelatin A | | | 32 | 32 | | |
| | hydrolyzed gelatin B | | | | | 16 | 16 |
| matrix-forming agent (mg) | glycine | 24 | | 24 | | 24 | |
| | mannitol | | 24 | | 24 | | 24 |
| | Purified water | 360 | 360 | 344 | 344 | 360 | 360 |

Note:
hydrolyzed gelatin A: obatined from Hangzhou Minsheng Gelatin Producing Co., ltd;
hydrolyzed gelatin B: obtained from Wenzhou Lucheng Gelatin Factory

TABLE 3

Weight Increased

| Time (day) | Example 24 Glycine Pullulan | Comparative example 1 Mannitol pullulan | Comparative example 2 Glycine Hydrolyzed gelatin | Comparative example 3 Mannitol Hydrolyzed gelation | Comparative example 4 Glycine Hydrolyzed gelain | Comparative example 5 Mannitol hydrolyzed gelatin |
|---|---|---|---|---|---|---|
| 0 | 0 | 0 | 0 | 0 | 0 | 0 |
| 1 | 2.00 | 4.14 | 7.8 | 7.9 | 5.10 | 5.12 |
| 2 | 2.13 | 4.27 | 7.9 | 8.2 | 5.18 | 5.20 |
| 3 | 2.13 | 4.35 | 8.0 | 8.4 | 5.20 | 2.23 |
| 4 | 2.16 | 4.48 | 8.4 | 8.7 | 5.25 | 5.30 |
| 5 | 2.17 | 4.56 | 8.4 | 8.8 | 5.27 | 5.32 |
| 6 | 2.17 | 4.61 | 8.5 | 8.8 | 5.30 | 5.36 |

As it could be seen from the test results of example 24 and comparative examples 1 to 5 shown in table 3, when the ratio of hydrolyzed gelatin as the binder increases (comparative examples 2 and 3), the hygroscopicity of formulation is the highest. When the content of hydrolyzed gelatin decreases, the hygroscopicity decreases obviously (the hygroscopicity decreases from about 7.8 to about 5.1 after one day). When pullulan is used in place of hydrolyzed gelatin as the binder, the hygroscopicity decreases continuously. According to the test results of example 24 and comparative examples 1, 4 and 5 where the amount of pullulan used is the same as that of hydrolyzed gelatin, the hygroscopicity of formulation prepared in comparative examples 4 and 5 were highest for using hydrolyzed gelatin. But it could be seen from the test results of comparative example 4 where glycine was used as the matrix-forming agent and comparative example 5 where mannitol was used as the matrix-forming agent, that the hygroscopicity of both formulations are nearly identical. As seen from the test results of example 24 where pullulan is used instead of hydrolyzed gelation and comparative example 1, the difference of hygroscopicity of the formulations prepared in example 24 and comparative example 1 is big. The hygroscopicity of the formulation using mannitol as the matrix-forming agent far exceeds that of the formulations using glycine as the matrix-forming agent (the hygroscopicity of the latter is only 2.00%, but the hygroscopicity of the former is as high as 4.14% after one day). Therefore, the hygroscopicity of the orally disintegrating formulation of the invention is very low, as shown by the test data of hygroscopicity.

TABLE 4

Appearance changes

| time | Example 24 | Comparative Example 1 | Comparative Example 2 | Comparative Example 3 | Comparative Example 4 | Comparative Example 5 |
|---|---|---|---|---|---|---|
| 0 | flat glossy and compact | flat glossy and compact | flat glossy and compact | flat glossy and compact | flat glossy and compact | flat glossy and compact |
| 1 | the change of appearance is not visible | Shrink and surface becomes uneven | Shrink and surface becomes uneven | Badly shrink and surface becomes uneven | Shrink and surface becomes uneven | Shrink and surface becomes uneven |
| 2 | the change of appearance nearly does | continuously shrinks and becomes an | continuously shrinks and becomes an | continuously shrinks and becomes an | continuously shrinks and becomes an | continuously shrinks and becomes an |

TABLE 4-continued

| | Appearance changes | | | | |
|---|---|---|---|---|---|
| time | Example 24 | Comparative Example 1 | Comparative Example 2 | Comparative Example 3 | Comparative Example 4 | Comparative Example 5 |
| | not occurs | unregular shape | unregular shape | more unregular shpe | unregular shape | unregular shape |

Note:
time unit: day

It could be seen from table 4, the appearance changes of the orally disintegrating formulation of the present invention were not observed and completely met the requirements of quality for drug after it was kept for one day under the definite condition, while the orally disintegrating formulations prepared by the method of the comparative examples 1 to 5 obviously shrinked after one day of the hygroscopicity test and its surface becomed uneven. It also could be seen from the test results of example 24 and comparative examples 1, 4 and 5 wherein pullulan and hydrolyzed gelatin in the same amount were used as the binder, that the hygroscopicity of the orally disintegrating formulation using hydrolyzed gelatin was the highest. It could be obtained from the test results after two days of the hygroscopicity test that the orally disintegrating formulation of comparative example 3 shrank continuously to a smaller size, and the formulations of comparative examples 1 to 5 shrank to a irregular shape and their appearance looked unpleasant, which does not comply with the quality requirement for product marketing.

It could be seen from the test results of above examples and comparative examples that the orally disintegrating formulation of the invention overcomes the drawbacks of the conventional technology, i.e. it is not necessary to take additional measures to control the moisture in the process of the formulation of the invention, thereby decreasing the cost and extending the shelf life because it does not absorb water even if subjected to foul conditions during preparation or store.

It should be noted that further modification of the invention herein disclosed will occur to those skilled in the relevant arts and all such modifications are deemed to be within the scope of the invention as defined by the appended claims.

We claim:

1. An orally disintegrating formulation comprising a drug and a matrix, wherein the matrix contains an amino acid and pullulan and the ratio by weight of the amino acid to pullulan is 0.1 to 10, wherein the amino acid is selected from the group consisting of glycine, serine, arginine and a combination thereof.

2. The orally disintegrating formulation according to claim 1, wherein the amino acid is glycine.

3. The orally disintegrating formulation according to claim 1, characterized in that it further comprises a thickening and suspending agent.

4. The orally disintegrating formulation according to claim 1, wherein the ratio by weight of the amino acid to pullulan is 0.17 to 5.5.

5. The orally disintegrating formulation according to claim 1, wherein the ratio by weight of the amino acid to pullulan is 0.5 to 1.5.

6. The orally disintegrating formulation according to claim 1, wherein the amino acid is serine.

7. The orally disintegrating formulation according to claim 1, wherein the amino acid is arginine.

* * * * *